United States Patent [19]

Greenstein

[11] Patent Number: 4,467,638

[45] Date of Patent: Aug. 28, 1984

[54] METHOD AND APPARATUS FOR QUANTITATIVELY EVALUATING THE SOLDERING PROPERTIES OF A WAVE SOLDERING SYSTEM

[75] Inventor: Bernard Greenstein, Hamilton, Ind.

[73] Assignee: RCA Corporation, New York, N.Y.

[21] Appl. No.: 494,287

[22] Filed: May 13, 1983

[51] Int. Cl.³ ............................................. G01N 13/00
[52] U.S. Cl. .................................. 73/64.4; 73/432 R; 228/103
[58] Field of Search ............... 73/64.4, 432 Z; 228/35, 228/56.5, 103, 104, 180 R; 29/593

[56] References Cited

U.S. PATENT DOCUMENTS 4,227,415 10/1980 Spirig ................................. 73/432 Z
4,409,333 10/1983 Tosima et al. ...................... 228/104

FOREIGN PATENT DOCUMENTS 16751 2/1980 Japan .................................. 228/103
82039 6/1980 Japan .................................. 73/64.4
97427 6/1982 Japan .................................. 73/64.4

Primary Examiner—Gerald Goldberg
Assistant Examiner—Hezron E. Williams
Attorney, Agent, or Firm—Birgit E. Morris; Edward J. Sites

[57] ABSTRACT

It has been found that the soldering properties of a wave soldering system can be quantitatively determined by measuring the wickability of the molten solder of the solder bath beyond the areas of direct immersion into the molten solder bath of a solder wave. The test is conducted by providing a test board having a pair of parallel strips of a solderable material such as copper. One of the parallel strips is formed in a continuous length. The other of the parallel strips is formed with discontinuity in the solderable material at regularly predetermined intervals along the length thereof. When conducting the test method of this invention, the test board is partially immersed into the solder wave in the same manner as a printed circuit board assembly, with the parallel strip being in alignment with the machine direction of the wave soldering apparatus. The test board is then removed from the solder wave. The point of maximum direct contact with the solder of the wave is determined from the discontinuous strip. The wickability on the other hand is determined by measuring the distance of the solder flow along the continuous strip from the point of immersion in the solder bath as indicated on the discontinuous strip. The length of travel of the solder on the continuous strip beyond the point of immersion into the molten solder pool is a direct quantitative measurement of the wickability which is directly related to the solderability of the wave soldering system.

12 Claims, 5 Drawing Figures

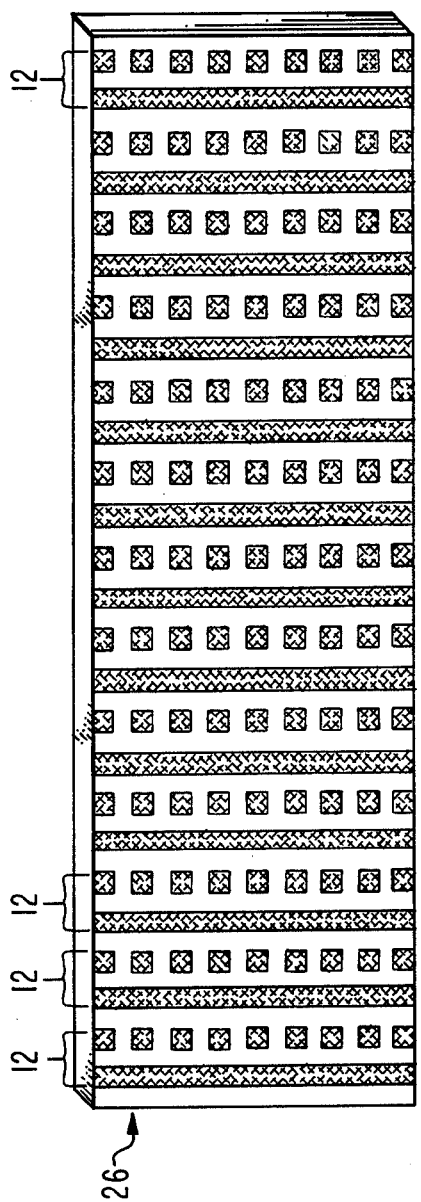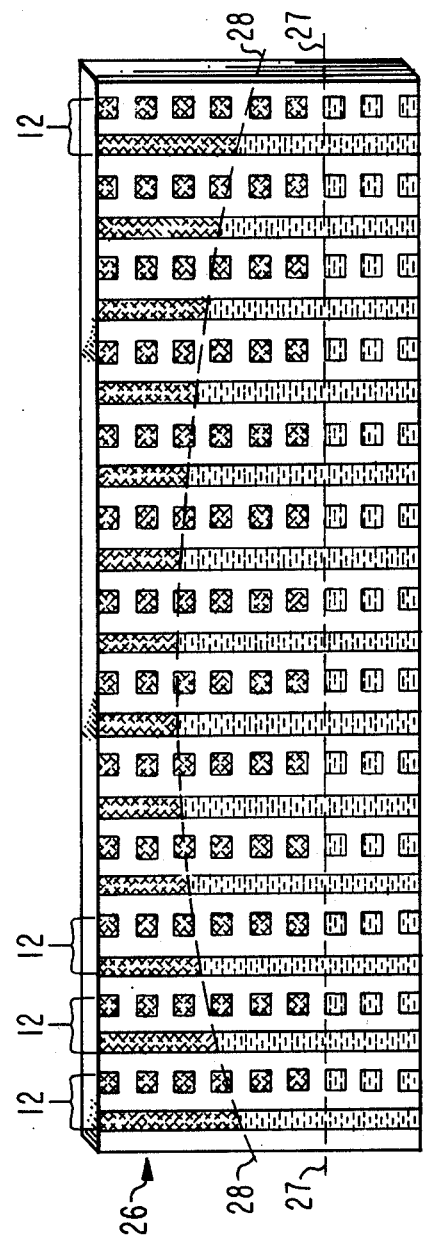

METHOD AND APPARATUS FOR QUANTITATIVELY EVALUATING THE SOLDERING PROPERTIES OF A WAVE SOLDERING SYSTEM

This invention relates to a method and apparatus for determining the soldering properties of a wave soldering system and more particularly is concerned with a quantitative method to evaluate the effect of process variables on the wave soldering of printed circuit board assemblies.

BACKGROUND OF THE INVENTION

Printed circuit board assemblies are used in the manufacture of a wide variety of electrical and electronic devices. The printed circuit board assemblies typically include a printed circuit board which has a core made of a dielectric material with a metal circuitry layer formed on one surface of the core. The printed circuit board assemblies also include leaded electronic components which are mounted on the upper surface of the printed circuit board, that is, the side opposite the surface on which the metal circuitry layer is formed, with the leads of the leaded components extending through the core to solder pads formed as part of the metal circuitry. Leadless electronic components are also mounted on the surface of the printed circuit board having the circuitry, with the terminals of the leadless components being in contact with solder pads of the metal circuitry.

In order to make the printed circuit board assemblies function satisfactorily it is necessary that electrical connections be made between the leads and terminals of the electronic components and the metal circuitry. The most effective method of making the required electrical connections is to solder the leads and terminals of the components to the circuitry. This can be done by individually hand soldering each lead and terminal, but this is highly impractical, especially in the commercial production of printed circuit board assemblies which may have literally hundreds of individual electrical connections on a single printed circuit board assembly.

Wave soldering is a technique which has been developed for mass soldering of printed circuit board assemblies in which the printed circuit board assemblies are soldered by passing the assembly with the metal circuitry side down through a standing wave of molten solder. The molten solder, under ideal conditions, should solder 100 percent of the leads and terminals to the circuitry. It has been found, however, that even under normally satisfactory operating conditions, considerable difficulties are often encountered in obtaining 100 percent soldering of the joints. The most common problem which occurs is that during wave soldering a number of connection points are not soldered. Part of the reasons for the problems is that there are a large number of process variables involved in wave soldering, many of which are interrelated and which can significantly and adversely affect solderability. These variables include the alloy composition of the solder, and more specifically, the presence and types of impurities in the solder composition, the temperature of the solder bath, the type and amount of flux utilized in the soldering process, the dynamics of the solder wave, the rate of travel of the printed circuit board assembly through the soldered wave, the placement of the electronic components and solder pads relative to the molten solder wave and other similar variables. In addition to the above noted variables, it is often found that there are process variations across the width of the solder wave which cause differences in the quality of the resulting solder connections in the cross machine direction.

Numerous test methods have heretofore been suggested to measure the process variables encountered in wave soldering. These test methods include chemical analysis of the solder composition to determine the alloy composition of the solder and the presence and amount of impurities and measurement of the surface tension and the temperature of the molten solder in the wave. Other variables which are regularly measured include, for example, the amount of flux and oil in the solder wave. The above noted tests at best, however, only give an indirect indication of whether satisfactory soldering can be obtained with a particular solder system.

A method which is commonly employed to directly evaluate the soldering properties of a given wave soldering system is to use unsoldered printed circuit board assemblies as test pieces and attempt to solder the printed circuit board assemblies in the wave soldering system to determine the soldering properties of the soldering system. The printed circuit board assemblies which are test soldered are examined to determine the relative number of the total connections that are correctly soldered. The use of printed circuit board assemblies as test pieces provides results which are directly related to the solderability of a given wave soldering system for a particular printed circuit board assembly but has several distinct disadvantages. Initially, it is an inherently expensive test method in that if satisfactory results are not immediately obtained on the first solder test, which rarely occurs, it can result in the waste of numerous high cost circuit board assemblies until the correct combination of soldering conditions is achieved. A further problem with directly testing soldering properties with unsoldered printed circuit board assemblies is that the results which are obtained are at best generally only indicative of the relative number of satisfactory solder joints obtained with a particular combination of soldering parameters. The test soldering of printed circuit board assemblies does not provide quantitative data which is highly desirable in order to establish how stable the molten solder bath system is with regard to conducting wave soldering of numerous printed circuit board assemblies. The quantitative evaluation of the soldering properties of a wave soldering system is extremely important especially when conducting relatively long soldering runs. It has been found that even if the soldering process parameters appear satisfactory on the test runs, it often happens when production scale soldering of printed circuit board assemblies is commenced, that extremely small changes in one or more of the process parameters, such as the solder temperature or the like, can occur which can cause an almost immediate shift in soldering properties and extremely poor soldering results. Accordingly, it is extremely important to have a quantitative evaluation of the relative stability of the wave soldering system so as to be able to predict the long range capability of the wave soldering system for use in commercial production of printed circuit board assemblies.

Printed circuit boards which have the required circuitry but which do not include the electronic components have also been utilized for the purpose of evaluating the soldering properties of wave solder systems.

The technique most commonly employed is to pass the printed circuit boards through the wave soldering apparatus in exactly the same manner as printed circuit board assemblies so as to obtain an indication of the solderability properties of the wave soldering system. The use of the printed circuit boards without the electronic components does substantially reduce the test cost. This technique, however, at best again only gives a result of the solderability of the board without components and the data for the printed circuit board have not always been found to be directly correlatable to the results obtained when soldering printed circuit board assemblies. The problem of the lack of correlation when using printed circuit boards is especially acute when the circuit board assembly to thereafter be soldered includes leadless components on the metal circuitry side.

What would be highly desirable would be a test method and apparatus which could evaluate quantitatively the soldering properties of a wave soldering system in a manner which would be both simple to conduct, relatively inexpensive and which would provide quantitative data directly related to the soldering properties of printed circuit board assemblies in the wave soldering system.

SUMMARY OF THE INVENTION

It has been found that the soldering properties of a wave soldering system can be quantitatively determined by measuring the wickability of the molten solder of the solder bath beyond the areas of direct immersion into the molten solder of the solder wave. The test for wickability is conducted by providing a test board having a pair of parallel strips of a solderable metal such as copper. One of the parallel strips is formed in a continuous length. The other of the parallel strips is formed with discontinuities in the solderable metal at regular predetermined intervals along the length of the strip. When conducting the test method of this invention, the test board is partially immersed into the solder wave in the same manner as a printed circuit board assembly with the parallel strip being in alignment with the machine direction of the wave soldering apparatus. The test board is then removed from the solder wave. The point of maximum direct contact with the solder of the wave is determined from the discontinuous strip. The wickability on the other hand is determined by measuring the distance of solder flow along the continuous strip from the point of immersion in the solder bath indicated on the discontinuous strip. The length of travel of the solder on the continuous strip beyond the point of immersion into the molten solder is a direct quantitative measurement of the wickability which is directly related to the solderability of the wave soldering system.

BRIEF DESCRIPTION OF THE DRAWING

FIG. 4 is a top plan illustration of an alternative type of test board having a plurality of test patterns spaced across the width of the board for testing cross machine solderability in accordance with the method of this invention.

FIG. 5 is an illustration of the test board of FIG. 4 after having been used in the solderability test method of the present invention.

DETAILED DESCRIPTION OF THE INVENTION

Figure 3:
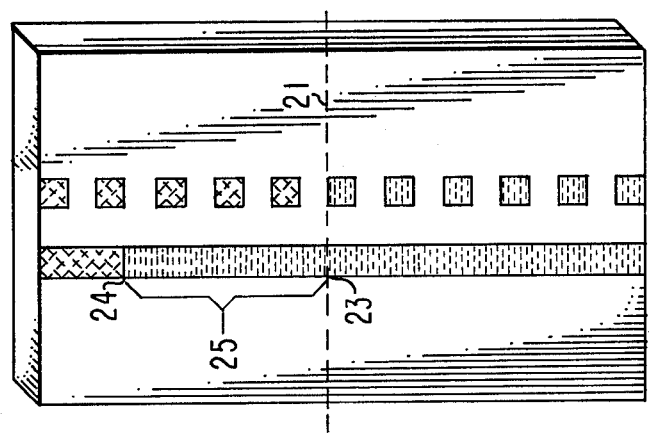
FIG. 3 is an illustration of the test board as illustrated in FIG. 1 after having been used in the evaluation method schematically illustrated in FIG. 2.

The test board 10 used in the method of this invention is a form of a printed circuit board. The test board 10 has a core 11 which is made of a dielectric material such as an epoxy glass laminate or the like. Most preferably the core 11 is made of the same material as that of the printed circuit board assembly (not shown) which will ultimately be soldered, as this eliminates a possible variable which can cause differences from the test results and the actual results obtained on the soldering of the printed circuit board assemblies.

On one of the surfaces of the core 11 of the test board 10 is formed a test pattern 12. The test pattern 12 is comprised of a pair of spaced apart parallel strips of a solderable metal. The first of the strips 13 is made in a continuous length. The second strip 14 is formed in a discontinuous length having spaced alternately areas 15 which are solderable and adjacent unsolderable areas 16. The distance between the solderable areas 15 and the unsolderable areas 16 should be at least sufficient to prevent bridging of solder between adjacent solderable areas. The solderable metal used to make the strips 13, 14 is preferably the same metal or metal alloy employed to form the circuitry of the printed circuit board assembly to be thereafter soldered. It has been found, however, that in practice copper is most preferably employed because of its good soldering properties and its wide and almost universal use in the printed circuit board assembly.

The pattern 12 can be formed on the surface of the test piece 10 by various conventional well known means. The most convenient methods to employ are to use photolithographic techniques to etch the pattern into a layer of metal or, in the alternative, to use a solder resist to expose only the pattern 12 of solderable metal. In order to have the closest correlation between the results obtained by the present method and those encountered in actual practice it is preferable that the method used to form the test pattern be similar to the method employed to form the printed circuit pattern on the printed circuit board assembly.

The width of the continuous parallel line 13 of the test pattern 12 is a relatively critical parameter. The reason for this is that the amount of wicking which occurs on soldering is related to the width of the test strip 13. In general, the narrower the test strip 13 the greater will be the total length of the solder that wicks along the test strip. In order to obtain data from the evaluation by the method of this invention which is comparable with actual production results, the test strip 13 should be approximately the width of the circuitry lines used on the printed board assemblies which are intended to be soldered, which is typically in the range between about 0.8 to 1.12 mm.

The overall size of the test piece is not critical with the exception that in the lengthwise direction, that is the machine direction as fed through the wave soldering apparatus, the test board 10 must be of sufficient length so as to be advanced partially into the solder wave for a substantial portion of the length so as to obtain reproducible test results but not so much as to cause the wicking along the continuous test strip 13 to continue to the opposite edge of the test board. In practice it has been found that test boards in the approximate size of about 5 cm in width and 10 cm in length are adequate for most testing purposes.

Figure 2:
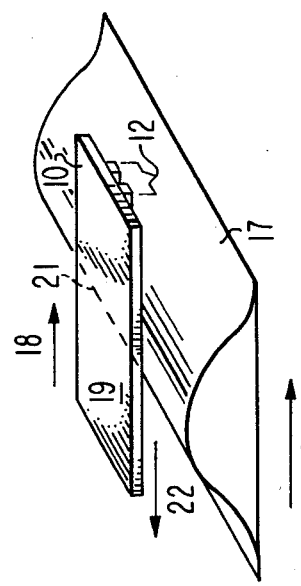
FIG. 2 is a schematic illustration of the method of evaluating solderability in accordance with the present invention.
Figure 1:
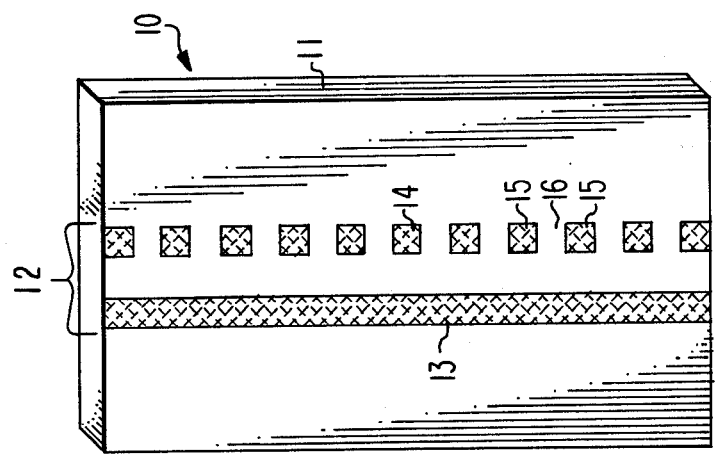
FIG. 1 is a top plan view of a test board for use in the method of this invention.

In accordance with the method of this invention, the solder system to be evaluated for use in the wave soldering of printed circuit board assemblies is set up within the control parameters anticipated to be suitable for the soldering operation. Once the wave soldering apparatus and particularly the solder wave itself has come into equilibrium, the test method of this invention is preformed. A test board 10 is advanced into the standing solder wave 17 of the soldering apparatus with the test pattern 12 on the bottom surface, preferably at the same rate of advance and angle of entry as is anticipated when the printed circuit board assemblies will be fed into the wave soldering apparatus. As shown in FIG. 2, the test board 10 is fed into the solder wave 17 in the machine direction 18 of the wave soldering apparatus. A substantial portion 19 of the test board 10 passes into the solder wave 17 and makes direct contact with the molten solder of the solder wave 17. Then, in accordance with this invention, the contact of the test board 10 with the solder wave 17 is discontinued at an intermediate point indicated by the dotted line 21 on FIG. 2. At this point, the travel of the test board 10 can be reversed so as to travel in the opposite direction as indicated by the arrow 22. A similar discontinuation of the solder contact, can likewise be obtained by dropping the solder wave 17 in the conventional manner known to those skilled in the art. The net result is that solder only contacts a portion 19 of the test board 10. The purpose of making this partial contact is to accurately determine exactly what portion of the test board 10 was actually contacted with molten solder. It can be appreciated that under the conditions of wave soldering, it would normally be extremely difficult, if not impossible, to accurately determine exactly the portion of the test board actually contacted by the molten solder of the solder wave 17. However, by using the test board 10 in this invention, it can be accurately determined by examining the wave soldered test board and particularly a second strip 14 of the test pattern 12. The solderable sections 15 of the discontinuous strip 14 which actually contacts the molten solder will have solder on the surfaces which is indicated by a change in the color from copper to silver white. The solderable portions 15, however, which do not actually enter the molten solder of the solder wave 17 will remain unchanged. The distinction between the portion of the board which actually enters the molten solder and the portion which does not is made possible by the unsolderable portions 16 between the solderable portions 15.

The determination of the point of maximum penetration 23 provides the initial point from which to determine the wickability of the solder of the solder system under evaluation. This is measured from the point of maximum immersion 23 of the solder by the first strip 13 as determined by the comparison with the second strip 14 of the pattern 12 as noted above. The amount of wickability is then determined by measuring the length from the point of immersion 23 to the point where the wicking terminates 24. The length of the wicking of copper quantitatively indicates the solderability of the solder system under evaluation. The longer the section 25 the better the relative soldering properties of the solder system under evaluation for soldering printed circuit boards.

While the exact reason for the direct relationship between the relative wickability and solderability for a printed circuit board is not known for certain, it is believed to be due to a combination of improved wetability and afterflow which causes the solder pads initially passed over by the solder wave to thereafter be soldered by solder wicked along the leadlines in much the way the solder is wicked along the solder strip 13.

The present invention is quite useful for quantitatively evaluating the solderability of a given soldering system, and is also highly useful in evaluating the effect of changes in the soldering parameter so as to obtain optimum solderability with a given soldering system.

An alternate embodiment of this invention enables one to make evaluations of the solderability in the cross machine direction of a wave soldering apparatus. For this purpose a modified test board 26 is provided which as a number of repeats of the test pattern 12 formed across the entire width of the test board 26.

The test piece 26 is used in much the same manner as that described above for the test piece 10 having a single test pattern 12. As before, the test board 26 is immersed into the solder wave 17. The line of direct contact of the solder of the solder wave 17 with the test board 26 is determined by observing the soldering of the portions of the strips 14 of the test patterns 12 on the board 26. In FIG. 5 this is illustrated by the line 27 to show the soldered sections of the discontinuous strip 14 of the test patterns 12. The cross machine pattern of solderability as it relates to wickability is then established by observing points of maximum travel along each of the continuous strips 13 of the test patterns 12 as indicated by the line 28. By evaluation of the test board illustrated in FIG. 5, corrections can be made in order to balance the cross machine variations in the wave 17 of a wave soldering machine.

What is claimed is:

1. A method for quantitatively evaluating the soldering properties of a soldering system which includes a molten solder wave for use in the soldering of a printed circuit board assembly having solderable circuitry, said method comprising;
   (a) providing a test board having a length and a width, said test board having defined on a surface thereof in the lengthwise direction a pattern comprised of first and second spaced apart and parallel strips of a solderable metal, said first strip being formed in a continuous length and said second strip being formed in a discontinuous length, having spaced alternative solderable areas and nonsolderable areas with the distance between the solderable areas and the nonsolderable areas being at least sufficient to prevent bridging of molten solder between the solderable areas;
   (b) positioning the test board with the length thereof in alignment with the direction of travel to be taken through the molten solder wave with the surface of the test board having the parallel strips defined thereon being on the underside thereof so as to contact the molten solder of the solder wave;
   (c) advancing the test board into the molten solder wave for a distance less than the entire length of the test board but sufficient for the solder of the solder wave to wet out the length immersed into the solder wave;
   (d) removing the test board from the molten solder of the solder wave;

(e) determining the approximate point of maximum contact of the molten solder of the solder wave with the test board; and (f) measuring the distance the solder wicked along the first strip beginning at the point of maximum direct contact of the molten solder with the test board as indicated by the second strip;

whereby the relative solderability properties of the soldering system can be directly determined by the length of wicking of the solder along the first strip from the point of direct contact with the molten solder of the solder wave.

2. The method according to claim 1 wherein the first and second strips of metal are comprised of the same metal as the circuitry of the printed circuit board assembly.

3. The method according to claim 1 wherein the solderable metal of the first and second strips are comprised of copper.

4. The method according to claim 1 wherein the test board has a core made of the same material as the core of the printed circuit board of the printed circuit board assembly.

5. The method according to claim 1 wherein the pattern formed in the test board is formed in the same manner as the circuitry of the printed circuit board assembly.

6. The method according to claim 1 wherein the pattern is formed by applying a solder resist over the areas not be soldered.

7. The method according to claim 1 wherein in said pattern is repeated a plurality of times across the width of the test board.

8. The method according to claim 7 wherein the width of the board is substantially the same as the width of the solder wave and wherein the test piece is partially immersed in the molten wave in the lengthwise direction and parallel to the molten solder wave and thereafter removed, whereby a cross machine variation is indicated on the test piece.

9. A test board for use in evaluating the soldering properties of a soldering system which includes a molten solder wave of a given width, said test board being comprised of a substrate having a length and a width having formed on the surface thereof a test pattern in the lengthwise direction comprised of first and second spaced apart parallel strips of a solderable metal, said first strip being continuous in length and said second strip being discontinuous in length and having spaced alternate solderable and nonsolderable areas with the distance between the solderable areas being at least sufficient to prevent bridging of molten solder from a solderable area contacted with the molten solder of the solder wave to the next adjacent solderable area which is not contacted with molten solder.

10. A test board according to claim 9 wherein the solderable metal is copper.

11. A test board according to claim 9 which includes a plurality of repeats of said pattern along the width of said board.

12. A test board according to claim 9 wherein the width of the test board is substantially the same as the given width of the solder wave and includes repeats of said pattern across the entire width of the board whereby the test board can be used to determine the cross machine solderability properties of the solder wave.

* * * * *